US009399662B2

(12) United States Patent
Sampson et al.

(10) Patent No.: US 9,399,662 B2
(45) Date of Patent: *Jul. 26, 2016

(54) CONCURRENT CHEMOTHERAPY AND IMMUNOTHERAPY

(75) Inventors: John H. Sampson, Durham, NC (US); Darell D. Bigner, Mebane, NC (US); Duane Mitchell, Durham, NC (US); Amy Heimberger, Houston, TX (US)

(73) Assignees: Duke University, Durham, NC (US); Board of Regents, The University of Texas System, Austin, TX (US)

( * ) Notice: Subject to any disclaimer, the term of this patent is extended or adjusted under 35 U.S.C. 154(b) by 1897 days.

This patent is subject to a terminal disclaimer.

(21) Appl. No.: 12/092,180

(22) PCT Filed: Nov. 2, 2006

(86) PCT No.: PCT/US2006/042812
§ 371 (c)(1),
(2), (4) Date: Nov. 21, 2008

(87) PCT Pub. No.: WO2007/056061
PCT Pub. Date: May 18, 2007

(65) Prior Publication Data
US 2009/0220551 A1 Sep. 3, 2009

Related U.S. Application Data

(60) Provisional application No. 60/732,741, filed on Nov. 2, 2005.

(51) Int. Cl.
*C07K 7/08* (2006.01)
*A61K 39/00* (2006.01)
*A61K 47/48* (2006.01)
*C07K 14/435* (2006.01)

(52) U.S. Cl.
CPC ............... *C07K 7/08* (2013.01); *A61K 39/0005* (2013.01); *A61K 39/0011* (2013.01); *A61K 47/48284* (2013.01); *C07K 14/43504* (2013.01); *A61K 2039/55522* (2013.01); *A61K 2039/6081* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,894,018 A | 4/1999 | Davila et al. | |
| 6,224,868 B1 * | 5/2001 | Wong et al. | 424/184.1 |
| 6,251,886 B1 * | 6/2001 | Friedman | 514/183 |
| 6,503,503 B1 | 1/2003 | Bigner et al. | |
| 6,645,503 B1 | 11/2003 | Arumugham et al. | |
| 2002/0155464 A1* | 10/2002 | Salceda et al. | 435/6 |
| 2004/0147428 A1* | 7/2004 | Pluenneke | 514/1 |
| 2005/0215501 A1* | 9/2005 | Lipford et al. | 514/44 |

FOREIGN PATENT DOCUMENTS

| | | |
|---|---|---|
| RU | 2245149 C2 | 1/2005 |
| WO | 99/06544 | 2/1999 |
| WO | 02/060484 | 8/2002 |
| WO | WO 03/080111 | 10/2003 |
| WO | 2004/026337 | 4/2004 |
| WO | 2005043155 A1 | 5/2005 |
| WO | 2005058940 A2 | 6/2005 |
| WO | 2005081854 A2 | 9/2005 |

OTHER PUBLICATIONS

Heimberger et al. (Clinical Cancer Research 2003; 9: 4247-4254).*
Heimberger et al. (Clinical Cancer Research 2003; 9: 4247-4254.*
Moscatello et al .(Cancer Research 1997; 57: 1419-1424).*
Terando et al. (Cancer Immunol. Immunother. 2003; 52: 680-685).*
Su et al .(Journal of Clinical Oncology, Feb. 2004; 22: 610-616).*
Carter, J.M. (The Protein Protocols Handbook. Princeton: Humana Press, 1996. pp. 689-692).*
Bartolomei et al (QJ Nucl MED, 48:220-228, 2004).*
Immunobiology 5 (Janeway et al, p. 610, 2001).*
Heimberger et al., "Epidermal Growth Factor Receptor VIII Peptide Vaccination is Efficacious Against Established Intracerebral Tumors," Clinical Cancer Research, Sep. 15, 2003, vol. 9, pp. 4247-4254.
C.-T. Kuan et al., "EGFRvIII As a Promising Target for Antibody-Based Brain Tumor Therapy," Brain Tumor Pathol (2000), 17:71-78.
Y. B. Su et al., "How Lymphotoxic is Dose-Intensified Temozolomide? The Glioblastoma Experience," Journal of Clinical Oncology, Jun. 20, 2005, vol. 22, No. 18, pp. 4235-4236.
Y. B. Su et al., "Selective CD4+ Lymphopenia i Melanoma Patients Treated with Temozolomide: A Toxicity with Therapeutic Implications," Journal of Clinical Oncology, Feb. 15, 2004, vol. 22, No. 4, pp. 610-616, and p. 2038.
R. B. Khan et al., "A Phase II Study of Extended Low-Dose Temozolomide in Recurrent Malignant Gliomas1,2," Neuro-Oncology, Jan. 2002, pp. 39-43.
J. H. Sampson et al., "Effect of EGFRvIII-Targeted Vaccine (CDX-110) on Immune Response and TTP When Given with Simultaneous Standard and Continuous Temozolomide in Patients with GBM,"American Society of Clinical Oncology, 2008, vol. 26, (May 20 suppl abstr 2011), 3 pages.

(Continued)

Primary Examiner — Brad Duffy
(74) Attorney, Agent, or Firm — Banner & Witcoff, LTD.

(57) ABSTRACT

The concurrent administration of chemotherapy and immunotherapy has been considered a contraindication because of the concern that the induced lymphopenia would ablate therapeutic efficacy of immunotherapy. Temozolomide has been shown to be an effective chemotherapeutic for patients with malignant gliomas and to deprive patients with glioblastoma (GBM) patients of this agent in order to treat with immunotherapy is controversial. Despite conventional dogma, we demonstrate that both chemotherapy and immunotherapy can be delivered concurrently without negating the effects of immunotherapy, hi fact, the temozolomide induced lymphopenia may actually be synergistic with a peptide vaccine.

2 Claims, No Drawings

(56) References Cited

OTHER PUBLICATIONS

A. B. Heimberger et al., Immunological Responses in a Patient with Glioblastoma Multiforme Treated with Sequential Courses of Temozolomide and Immunotherapy: Case Study, Neuro-Oncology, Feb. 2008, pp. 98-103.

B. Goldman, "An Injection of Hope," The Journal of Life Sciences, Oct. 2007, 8 pages.

J. H. Sampson et al., "Epidermal Growth Factor Receptor Variant III (EGFRvIII)-Targeted Vaccine (CDX-110/PF-04948568) in GBM." Abstract only.

A. Terando et al., "On Combining Antineoplastic Drugs With Tumor Vaccines," Cancer Immunology Immunotherapy, Nov. 2003, vol. 52, No. 11, pp. 680-685.

Wachi, K. et al.; "T-Cell lymphopenia associated with infliximab and cyclophosphamide."; American Journal of Medical Sciences; Jul. 2005; vol. 330; No. 1; abstract.

Japanese Office Action issued in related Japanese Application No. 2008-539027, dated Oct. 15, 2012.

Korean Office Action issued in related Korean Application No. 10-2008-7012182, dated May 16, 2013.

Japanese Office Action issued in related Japanese Application No. 2013-025374, dated Apr. 2, 2014.

Wheeler et al., "Clinical Responsiveness of Glioblastoma Multiforme to Chemotherapy after Vaccination," Clinical Cancer Research, 2004, 10:5316-5326.

Office Action issued in related U.S Appl. No. 14/564,132, mailed on Nov. 30, 2015.

Dummer et al. (JCI, 110:185-192, 2002).

Kuan et al., (ERC:8:83-96, 2001).

Sok et al. (CCR, 12(17):5064-5073, Sep. 1, 2006).

* cited by examiner

SEQUENCE LISTING

```
<160> NUMBER OF SEQ ID NOS: 9

<210> SEQ ID NO 1
<211> LENGTH: 14
<212> TYPE: PRT
<213> ORGANISM: Homo sapiens

<400> SEQUENCE: 1

Leu Glu Glu Lys Lys Gly Asn Tyr Val Val Thr Asp His Ser
 1               5                  10
```

<210> SEQ ID NO 2
<211> LENGTH: 13
<212> TYPE: PRT
<213> ORGANISM: Homo sapiens

<400> SEQUENCE: 2

Leu Glu Glu Lys Lys Gly Asn Tyr Val Val Thr Asp His
1               5                   10

<210> SEQ ID NO 3
<211> LENGTH: 14
<212> TYPE: PRT
<213> ORGANISM: Homo sapiens

<400> SEQUENCE: 3

Leu Glu Glu Lys Lys Gly Asn Tyr Val Val Thr Asp His Cys
1               5                   10

<210> SEQ ID NO 4
<211> LENGTH: 14
<212> TYPE: PRT
<213> ORGANISM: Homo sapiens

<400> SEQUENCE: 4

His Asp Thr Val Tyr Cys Val Lys Gly Asn Lys Glu Leu Glu
1               5                   10

<210> SEQ ID NO 5
<211> LENGTH: 14
<212> TYPE: PRT
<213> ORGANISM: Homo sapiens

<400> SEQUENCE: 5

Gln Tyr Ile Lys Ala Asn Ser Lys Phe Ile Gly Ile Thr Glu
1               5                   10

<210> SEQ ID NO 6
<211> LENGTH: 1210
<212> TYPE: PRT
<213> ORGANISM: Homo sapiens

<400> SEQUENCE: 6

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
        130                 135                 140

His Gly Ala Val Arg Phe Ser Asn Asn Pro Ala Leu Cys Asn Val Glu

```
            145                 150                 155                 160
        Ser Ile Gln Trp Arg Asp Ile Val Ser Ser Asp Phe Leu Ser Asn Met
                        165                 170                 175

Ser Met Asp Phe Gln Asn His Leu Gly Ser Cys Gln Lys Cys Asp Pro
                        180                 185                 190

Ser Cys Pro Asn Gly Ser Cys Trp Gly Ala Gly Glu Asn Cys Gln
                    195                 200                 205

Lys Leu Thr Lys Ile Ile Cys Ala Gln Gln Cys Ser Gly Arg Cys Arg
            210                 215                 220

Gly Lys Ser Pro Ser Asp Cys Cys His Asn Gln Cys Ala Ala Gly Cys
        225                 230                 235                 240

Thr Gly Pro Arg Glu Ser Asp Cys Leu Val Cys Arg Lys Phe Arg Asp
                        245                 250                 255

Glu Ala Thr Cys Lys Asp Thr Cys Pro Pro Leu Met Leu Tyr Asn Pro
                    260                 265                 270

Thr Thr Tyr Gln Met Asp Val Asn Pro Glu Gly Lys Tyr Ser Phe Gly
                    275                 280                 285

Ala Thr Cys Val Lys Lys Cys Pro Arg Asn Tyr Val Val Thr Asp His
                290                 295                 300

Gly Ser Cys Val Arg Ala Cys Gly Ala Asp Ser Tyr Glu Met Glu Glu
        305                 310                 315                 320

Asp Gly Val Arg Lys Cys Lys Lys Cys Glu Gly Pro Cys Arg Lys Val
                        325                 330                 335

Cys Asn Gly Ile Gly Ile Gly Glu Phe Lys Asp Ser Leu Ser Ile Asn
                    340                 345                 350

Ala Thr Asn Ile Lys His Phe Lys Asn Cys Thr Ser Ile Ser Gly Asp
                    355                 360                 365

Leu His Ile Leu Pro Val Ala Phe Arg Gly Asp Ser Phe Thr His Thr
                370                 375                 380

Pro Pro Leu Asp Pro Gln Glu Leu Asp Ile Leu Lys Thr Val Lys Glu
        385                 390                 395                 400

Ile Thr Gly Phe Leu Leu Ile Gln Ala Trp Pro Glu Asn Arg Thr Asp
                        405                 410                 415

Leu His Ala Phe Glu Asn Leu Glu Ile Ile Arg Gly Arg Thr Lys Gln
                    420                 425                 430

His Gly Gln Phe Ser Leu Ala Val Val Ser Leu Asn Ile Thr Ser Leu
                    435                 440                 445

Gly Leu Arg Ser Leu Lys Glu Ile Ser Asp Gly Asp Val Ile Ile Ser
        450                 455                 460

Gly Asn Lys Asn Leu Cys Tyr Ala Asn Thr Ile Asn Trp Lys Lys Leu
        465                 470                 475                 480

Phe Gly Thr Ser Gly Gln Lys Thr Lys Ile Ile Ser Asn Arg Gly Glu
                        485                 490                 495

Asn Ser Cys Lys Ala Thr Gly Gln Val Cys His Ala Leu Cys Ser Pro
                    500                 505                 510

Glu Gly Cys Trp Gly Pro Glu Pro Arg Asp Cys Val Ser Cys Arg Asn
                515                 520                 525

Val Ser Arg Gly Arg Glu Cys Val Asp Lys Cys Asn Leu Leu Glu Gly
                    530                 535                 540

Glu Pro Arg Glu Phe Val Glu Asn Ser Glu Cys Ile Gln Cys His Pro
        545                 550                 555                 560

Glu Cys Leu Pro Gln Ala Met Asn Ile Thr Cys Thr Gly Arg Gly Pro
                        565                 570                 575
```

```
Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990
```

Thr Asp Ser Asn Phe Tyr Arg Ala Leu Met Asp Glu Glu Asp Met Asp
        995                1000               1005

Asp Val Val Asp Ala Asp Glu Tyr Leu Ile Pro Gln Gln Gly Phe Phe
    1010               1015               1020

Ser Ser Pro Ser Thr Ser Arg Thr Pro Leu Leu Ser Ser Leu Ser Ala
1025               1030               1035               1040

Thr Ser Asn Asn Ser Thr Val Ala Cys Ile Asp Arg Asn Gly Leu Gln
        1045               1050               1055

Ser Cys Pro Ile Lys Glu Asp Ser Phe Leu Gln Arg Tyr Ser Ser Asp
        1060               1065               1070

Pro Thr Gly Ala Leu Thr Glu Asp Ser Ile Asp Asp Thr Phe Leu Pro
        1075               1080               1085

Val Pro Glu Tyr Ile Asn Gln Ser Val Pro Lys Arg Pro Ala Gly Ser
        1090               1095               1100

Val Gln Asn Pro Val Tyr His Asn Gln Pro Leu Asn Pro Ala Pro Ser
1105               1110               1115               1120

Arg Asp Pro His Tyr Gln Asp Pro His Ser Thr Ala Val Gly Asn Pro
        1125               1130               1135

Glu Tyr Leu Asn Thr Val Gln Pro Thr Cys Val Asn Ser Thr Phe Asp
        1140               1145               1150

Ser Pro Ala His Trp Ala Gln Lys Gly Ser His Gln Ile Ser Leu Asp
        1155               1160               1165

Asn Pro Asp Tyr Gln Gln Asp Phe Phe Pro Lys Glu Ala Lys Pro Asn
        1170               1175               1180

Gly Ile Phe Lys Gly Ser Thr Ala Glu Asn Ala Glu Tyr Leu Arg Val
1185               1190               1195               1200

Ala Pro Gln Ser Ser Glu Phe Ile Gly Ala
                1205               1210

<210> SEQ ID NO 7
<211> LENGTH: 628
<212> TYPE: PRT
<213> ORGANISM: Homo sapiens

<400> SEQUENCE: 7

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

```
Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575
```

```
Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Ser
625

<210> SEQ ID NO 8
<211> LENGTH: 405
<212> TYPE: PRT
<213> ORGANISM: Homo sapiens

<400> SEQUENCE: 8

Met Arg Pro Ser Gly Thr Ala Gly Ala Ala Leu Leu Ala Leu Leu Ala
  1               5                  10                  15

Ala Leu Cys Pro Ala Ser Arg Ala Leu Glu Glu Lys Lys Val Cys Gln
             20                  25                  30

Gly Thr Ser Asn Lys Leu Thr Gln Leu Gly Thr Phe Glu Asp His Phe
         35                  40                  45

Leu Ser Leu Gln Arg Met Phe Asn Asn Cys Glu Val Val Leu Gly Asn
     50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320
```

```
Asp Gly Val Arg Lys Cys Lys Cys Glu Gly Pro Cys Arg Lys Val
            325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Leu Ser
            405

<210> SEQ ID NO 9
<211> LENGTH: 405
<212> TYPE: PRT
<213> ORGANISM: Homo sapiens

<400> SEQUENCE: 9

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
            85                  90                  95

Glu Arg Ile Pro Leu Glu Asn Leu Gln Ile Ile Arg Gly Asn Met Tyr
        100                 105                 110

Tyr Glu Asn Ser Tyr Ala Leu Ala Val Leu Ser Asn Tyr Asp Ala Asn
    115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
            165                 170                 175

Ser Met Asp Phe Gln Asn His Leu Gly Ser Cys Gln Lys Cys Asp Pro
        180                 185                 190

Ser Cys Pro Asn Gly Ser Cys Trp Gly Ala Gly Glu Glu Asn Cys Gln
    195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
            245                 250                 255

Glu Ala Thr Cys Lys Asp Thr Cys Pro Pro Leu Met Leu Tyr Asn Pro
        260                 265                 270

Thr Thr Tyr Gln Met Asp Val Asn Pro Glu Gly Lys Tyr Ser Phe Gly
```

-continued

```
         275                 280                 285
Ala Thr Cys Val Lys Lys Cys Pro Arg Asn Tyr Val Val Thr Asp His
     290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
             340                 345                 350

Ala Thr Asn Ile Lys His Phe Lys Asn Cys Thr Ser Ile Ser Gly Asp
         355                 360                 365

Leu His Ile Leu Pro Val Ala Phe Arg Gly Asp Ser Phe Thr His Thr
     370                 375                 380

Pro Pro Leu Asp Pro Gln Glu Leu Asp Ile Leu Lys Thr Val Lys Glu
385                 390                 395                 400

Ile Thr Gly Leu Ser
            405
```

CONCURRENT CHEMOTHERAPY AND IMMUNOTHERAPY

This application claims the benefit of U.S. provisional application 60/732,741 filed Nov. 2, 2005, the entire contents of which are expressly incorporated herein.

This invention was made with support from the U.S. government under Grant No. R01CA097222 from the National Institutes of Health. The U.S. government therefore retains certain rights to this invention.

TECHNICAL FIELD OF THE INVENTION

This invention is related to the area of cancer immunotherapy. In particular, it relates to enhancing response to tumor vaccines.

BACKGROUND OF THE INVENTION

Despite aggressive surgical resection, high-dose focused radiation therapy, and chemotherapy, patients diagnosed with GBM have a median survival of less than 15 months after diagnosis (Stupp et al., Optimal role of temozolomide in the treatment of malignant gliomas. Curr Neurol Neurosci Rep. 2005 May; 5(3):198-206). Failure of therapy can be attributed, at least in part, to a relatively narrow therapeutic index so that attempts at dose escalation results in dose-limiting systemic or neurological toxicity. The use of immunotherapy has held promise for the potential treatment of these tumors but until recently, few have demonstrated clinical efficacy. Several clinical trials, with selected patients, involving vaccination of glioma patients with dendritic cells (DCs) and either acid-eluted peptides (Ashkenazi et al., A selective impairment of the IL-2 system in lymphocytes of patients with glioblastomas: increased level of soluble IL-2R and reduced protein tyrosine phosphorylation. Neuroimmunomodulation. 1997; Kolenko et al., Tumor-induced suppression of T lymphocyte proliferation coincides with inhibition of Jak3 expression and IL-2 receptor signaling: role of soluble products from human renal cell carcinomas. J Immunol. 1997 Sep. 15; 159(6):3057-67; Liau et al., Dendritic cell vaccination in glioblastoma patients induces systemic and intracranial T-cell responses modulated by the local central nervous system tumor microenvironment. Clin Cancer Res. 2005 Aug. 1; 11(15):5515-25) or an antigen-specific peptide (Heimberger A B, Archer G E, et al., Dendritic cells pulsed with a tumor-specific peptide induce long-lasting immunity and are effective against murine intracerebral melanoma. Neurosurgery. 2002 January; 50(1):158-64; discussion 164-6) have demonstrated promise by increasing median survival time to a range of 20-31 months. Furthermore, in a recently completed phase II clinical trial utilizing an antigen-specific immunotherapeutic approach, time to progression (TTP) in GBM patients was delayed to 15 months, which is in marked contrast to the standard of care consisting of radiotherapy and temozolomide that had a TTP of 7 months (Stupp et al., 2005, supra), and median survival was 29 months (Heimberger et al, J Transl Med. 2005 Oct. 19; 3:38 The natural history of EGFR and EGFRvIII in glioblastoma patients.). Cumulatively, these immunotherapy trials suggest that despite the inherent immunosuppression of malignant glioma patients, efficacious immune responses can be generated. However, there is reluctance to not treat GBM patients with some form of chemotherapy given the recently established standard of care and the overall poor prognosis.

There is a continuing need in the art to develop better methods for treating tumors in general and glioblastomas in particular.

SUMMARY OF THE INVENTION

A method is provided for treating a tumor in a subject. A treatment-effective amount of an EGFRvIII peptide and a treatment-effective amount of a chemotherapeutic agent which induces lymphopenia are administered to the subject.

According to another embodiment a method is provided for treating a tumor in a subject. A treatment-effective amount of an EGFRvIII peptide conjugated to KLH is administered to the subject with the tumor. Granulocyte/macrophage colony stimulating factor (GM-CSF) is also administered as an adjuvant in an effective amount concurrently with the EGFRvIII peptide. A treatment-effective amount of an alkylating agent is also administered to the subject.

According to still another embodiment, a method is provided for treating a tumor in a subject. A treatment-effective amount of an anti-tumor vaccine and a treatment-effective amount of temozolomide or a pharmaceutically acceptable salt thereof are administered to the subject.

According to still another embodiment, a method is provided for treating a tumor in a subject. A treatment-effective amount of an anti-tumor vaccine and a treatment-effective amount of a chemotherapeutic agent which induces lymphopenia are administered to the subject.

These and other embodiments which will be apparent to those of skill in the art upon reading the specification provide the art with additional methods for treating treatment-refractory tumors.

DETAILED DESCRIPTION OF THE INVENTION

The concurrent administration of chemotherapy and immunotherapy has been considered a contraindication because of the concern that the chemotherapy-induced lymphopenia would ablate therapeutic efficacy of immunotherapy. Temozolomide has been shown to be an effective chemotherapeutic for patients with malignant gliomas and to deprive patients with glioblastoma (GBM) patients of this agent in order to treat with immunotherapy is controversial. Despite conventional dogma, the inventors demonstrate that both chemotherapy and immunotherapy can be delivered concurrently without negating the effects of immunotherapy. In fact, the temozolomide induced lymphopenia may actually be synergistic with a peptide vaccine. Although applicants do not wish to be bound by any particular theory regarding mechanism of action, the observed synergy may be secondary to inhibition of Tregs or the failure to recover of Tregs, which permits an increase of effector cytotoxic $CD8^+$ T cells. Other mechanisms may also be involved.

"EGFRvIII" or "Epidermal Growth Factor Receptor mutation III" is a known mutant form of the Epidermal Growth Factor Receptor. See, e.g., U.S. Pat. No. 6,503,503; see also U.S. Pat. Nos. 6,900,221; 6,673,602; 6,479,286; and 6,129,915. The mutation which causes the production of the vIII protein is typically characterized by a consistent and tumor-specific in-frame deletion of 801 base pairs from the extracellular domain that splits a codon and produces a novel glycine at the fusion junction.

"EGFRvIII peptide", as used herein refers to a peptide of suitable length, e.g., at least 10 or 12 amino acids, and up to 16, 20 or 30 amino acids, or more, which spans the mutated splice junction of the corresponding EGFRvIII protein. Examples include but are not limited to: H-LEEKKGNYV- VTDHS-OH (SEQ ID NO: 1, or "PEP-3." The EGFRvIII peptide may be from (or correspond in sequence to) the EGFRvIII of any mammalian species, but is preferably human. Particular wild-type sequences of EGFR are shown in SEQ ID NO: 6 to 9.

"Carrier protein" as used herein refers to a protein which does not possess high homology to a protein found in the species that is receiving a composition of the invention and elicits an immune response. A protein possesses high homology if it is at least 75% identical, more preferably at least 85% identical or at least 90% identical to a protein as determined by any known mathematical algorithm utilized for the comparison of two amino acid sequences (see, e.g., Karlin and Altschul, 1990, Proc. Natl. Acad. Sci. USA 87: 2264-2268; Karlin and Altschul, 1993, Proc. Natl. Acad. Sci. USA 90: 5873-5877; Torellis and Robotti, 1994, Comput. Appl. Biosci. 10: 3-5; and Pearson and Lipman, 1988, Proc. Natl. Acad. Sci. 85: 2444-8). Preferably, the percent identity of two amino acid sequences is determined by BLAST protein searches with the XBLAST program, score=50, word length=3. Examples of heterologous carrier proteins include, but are not limited to, KLH, PhoE, mLT, TraT, or gD from BhV-1 virus. See, e.g., U.S. Pat. No. 6,887,472. Such carrier proteins may be conjugated or linked to the tumor antigen directly or by an intervening linker segment such as a chain of one or more (e.g., 2, 4, 6) intervening amino acids (e.g., an intervening CYS residue) in accordance with known techniques.

"KLH" or "keyhole-limpet hemocyanin" is a known carrier protein to which another protein may be conjugated in accordance with known techniques. See, e.g., U.S. Pat. No. 6,911,204.

"Adjuvant" as used herein refers to anyone of a diverse class of compounds that enhance the therapeutic efficacy of a vaccine which is administered concurrently with the adjuvant. In some embodiments the adjuvant is a hematopoietic growth factor such as GM-CSF. Common examples of adjuvants include but are not limited to aluminium hydroxide, -phosphate or -oxide, oil-in-water or water-in-oil emulsion based on, for example a mineral oil, such as Bayol Fo or Marcol 52TM or a vegetable oil such as vitamin E acetate, saponins, BCG, *M. vaccae*, Tetanus toxoid, Diphtheria toxoid, *Bordetella pertussis*, interleukin 2, interleukin 12, interleukin 4, interleukin 7, Complete Freund's Adjuvant, Incomplete Freund's Adjuvant, and a nonspecific adjuvant. See, e.g., U.S. Pat. No. 6,699,483.

"Hematopoietic growth factors" or "HGFS" are known. See, e.g., U.S. Pat. No. 6,863,885. In general, HGFs are glycoprotein cytokines that regulate the proliferation and differentiation of hematopoietic progenitor cells. The hematopoietic growth factors intended to be used in the present invention can be selected from the group G-CSF (granulocyte colony stimulating factor), SCF (stem cell factor), GM-CSF (granulocyte macrophage colony stimulating factor), IL-1 (interleukin-1), IL-3, IL-6, IL-8, IL-11, IL-12, LIF (leukemia inhibitory factor), FGF-beta (fibroblast growth factor beta), FLT3, or a combination thereof. These growth factors can be purchased (e.g., R&D Systems, Minneapolis, Minn.) or made following procedures set forth in the art generally and in publications describing the factors. Additionally, the hematopoietic growth factor can be a modified form of the factor or a fusion protein of hematopoietic growth factors selected from the group GCSF, SCF, GM-CSF, IL-1, IL-3, IL-6, IL-8, IL-11, IL-12, LIF, FGF-beta, and FLT3. HGFs include modified growth factors (e.g., muteins) and fusion proteins, which can be made according to methods known in the art. See, e.g. (Sambrook et al., Molecular Cloning: A Laboratory Manual, 2nd Ed., Cold Spring Harbor Laboratory, Cold Spring Harbor, N.Y., 1989). Hematopoietic growth factors that stimulate macrophage function such as GM-CSF are particularly preferred. These can be used as adjuvants.

"External beam radiotherapy" can be carried out by delivering a beam of high-energy x-rays to the location of the patient's tumor. The beam is generated outside the patient and is targeted at the tumor site. No radioactive sources are placed inside the patient's body. This can be used in conjunction with any other treatment step according to the invention.

"Treat" as used herein refers to any type of treatment or prevention that imparts a benefit to a subject afflicted with a disease or at risk of developing the disease, including improvement in the condition of the subject (e.g., in one or more symptoms), delay in the progression of the disease, delay the onset of symptoms or slow the progression of symptoms, etc. As such, the term "treatment" also includes prophylactic treatment of the subject to prevent the onset of symptoms.

As used herein, "treatment" and "prevention" are not meant to imply cure or complete ablatement of symptoms. Rather, these refer to any type of treatment that imparts a benefit to a patient afflicted with a disease, including improvement in the condition of the patient (e.g., in one or more symptoms), delay in the progression of the disease, etc.

"Treatment-effective amount" as used herein means an amount of the immunotherapeutic agent sufficient to produce a desirable effect upon a patient inflicted with cancer such as gliomblastoma, including improvement in the condition of the patient (e.g., in one or more symptoms), delay in the progression of the disease, etc.

Subjects in need of treatment by the methods described herein include subjects afflicted with glioblastoma or astrocytoma, as well as subjects afflicted with other solid tumors or cancers such as lung, colon, breast, brain, liver, prostate, spleen, muscle, ovary, pancreas, head and neck, skin (including melanoma), etc. Subjects in need of treatment particularly include subjects afflicted with a tumor, such as a brain tumor, that expresses EGFRvIII. The tumor may be a primary tumor, a metastatic tumor, or a recurrent tumor. Subjects to be treated by the methods of the invention particularly include subjects afflicted with a tumor expressing EGFRvIII, including gliomas, fibrosarcomas, osteosarcomas, melanoma, Wilms tumor, colon carcinoma, mammary and lung carcinomas, and squamous carcinomas. Subjects to be treated by the present invention most particularly include subjects afflicted with brain tumors or cancers, such as glioblastomas, particularly glioblastoma multiforme, and cystic astrocytoma.

The present invention is primarily concerned with the treatment of human subjects, including male and female subjects and neonatal, infant, juvenile, adolescent, adult, and geriatric subjects, but the invention may also be carried out on animal subjects, particularly mammalian subjects such as mice, rats, dogs, cats, livestock and horses for veterinary purposes, and for drug screening and drug development purposes.

The pharmaceutical compositions of the invention can be prepared in accordance with known techniques. Typically, the active agents are included in a pharmaceutically acceptable carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The compositions and methods of the invention may include the administration of one or more co-adjuvants. Suitable co-adjuvants include, but are not limited to: (1) aluminum salts (alum), such as aluminum hydroxide, aluminum phosphate, aluminum sulfate, etc.; (2) oil-inwater emulsion formulations (with or without other specific immunostimulating agents such as muramyl peptides (see below) or bacterial cell wall components), such as for example (a) MF59 (PCT Publication No. WO 90/14837), containing 5% Squalene, 0.5% Tween 80, and 0.5% Span 85 formulated into submicron particles, (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™) (for a further discussion of suitable submicron oil-in-water emulsions for use herein, see PCT Publication No. WO 99/30739, published Jun. 24, 1999); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CF A) and Incomplete Freunds Adjuvant (IF A); (5) cytokines, such as interleukins (IL-1, IL-2, etc.), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an E. coli heat-labile toxin (LT), particularly LT-K63 (where lysine is substituted for the wild-type amino acid at position 63) LT-R72 (where arginine is substituted for the wild-type amino acid at position 72), CT-SI09 (where serine is substituted for the wild-type amino acid at position 109), adjuvants derived from the CpG family of molecules, CpG dinucleotides and synthetic oligonucleotides which comprise CpG motifs (see, e.g., Krieg et al., Nature, 374:546 (1995) and Davis et al., J. Immunol., 160:870-876 (1998)) and PT-K9/GI29 (where lysine is substituted for the wild-type amino acid at position 9 and glycine substituted at position 129) (see, e.g., PCT Publication Nos. WO93/13202 and WO92/19265); (7) other substances that act as immunostimulating agents to enhance the effectiveness of the composition. See, e.g., U.S. Pat. No. 6,534,064; and (8) other ligands for Toll-like receptors in addition to CpG and RIBI adjuvants, such as bacterial flagellin (an effective adjuvant for CD4+ T cells; see IJ Immunol. 169: 3914-9 (October 2002).

The active agents may be administered by any medically appropriate procedure, e.g., normal intravenous or intra-arterial administration, injection into the cerebrospinal fluid). In certain cases, intradermal, intracavity, intrathecal or direct administration to the tumor or to an artery supplying the tumor is advantageous. Where the tumor or a portion thereof has been previously surgically removed the treatment agents may be administered into the site of the tumor (and particularly into an enclosed cavity or "resection cavity" at the site of the tumor) by direct injection or through a pre-implanted reservoir.

Dosage of the active agents will depend on, among other things, the condition of the subject, the particular category or type of cancer being treated, the route of administration, the nature of the therapeutic agent employed, and the sensitivity of the tumor to the particular therapeutic agent.

In general, the dose of the tumor antigen or vaccine, such as EGFRvIII, including any carrier protein or peptide conjugated thereto, will be from 10, 100 or 500 µg up to 2 or 3 mg per subject, for each dose. Doses may be given on a single occasion, optionally including follow-up or "booster" doses (e.g., one, two or three follow up or "booster" dosages given at intervals of from one to three weeks). Note that doses can be divided, such as administering to different injection sites, to reduce side effects such as local responses, if desired. Where the formulation contains both tumor antigen bound (or "conjugated") to the carrier protein and tumor antigen free of the carrier protein, the calculated dosage can include both the amount of both bound and free tumor antigen and carrier protein.

In general, the dose of the adjuvant such as GM-CSF will also be from 10 or 20 µg up to 500 µg, or 1 or 2 mg per subject, administered on the same schedule or different schedule from the dose of the tumor antigen. When administered on the same schedule the adjuvant may be administered in the same carrier as the tumor antigen. When not combined in the same carrier, the dose of adjuvant need only be administered sufficiently close in time to the dose of tumor antigen to enhance the efficacy thereof (e.g., within one or two hours; on the same day; etc.).

Alkylating agents useful for carrying out the present invention include (but are not limited to) 1,3-bis(2-chloroethyl)-1-nitrosourea (BCNU) and tetrazine derivatives, particularly [3H]imidazo[5,1-d]1,2,3,5-tetrazin-4-one derivatives such as temozolomide and analogs thereof (including pharmaceutically acceptable salts and pro drugs thereof). Such compounds are known. See, e.g., U.S. Pat. Nos. 6,096,724; 6,844,434; and 5,260,291. Examples of alkylating agents useful for carrying out the present invention include [3H]imidazo[5,1-d]-1,2,3,5-tetrazin-4-ones alkylating agents, particularly those of the general formula:

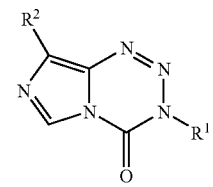

wherein $R^1$ represents a hydrogen atom, or a straight- or branched-chain alkyl, alkenyl or alkynyl group containing up to 6 carbon atoms, each such group being unsubstituted or substituted by from one to three substituents selected from halogen (i.e. bromine, iodine or, preferably, chlorine or fluorine) atoms, straight- or branched-chain alkoxy, (e.g. methoxy), alkylthio, alkylsullihinyl and alkylsulphonyl groups containing up to 4 carbon atoms, and optionally substituted phenyl groups, or $R^1$ represents a cycloalkyl group, and $R^2$ represents a carbamoyl group which may carryon the nitrogen atom one or two groups selected from straight- and branched-chain alkyl and alkenyl groups, each containing up to 4 carbon atoms, and cycloalkyl groups, e.g., a methylcarbamoyl or dimethylcarbamoyl group. When the symbol $R^1$ represents an alkyl, alkenyl or alkynyl group substituted by two or three halogen atoms, the aforesaid halogen atoms may be the same or different. When the symbol $R^1$ represents an alkyl, alkenyl or alkynyl group substituted by one, two or three optionally substituted phenyl groups the optional substituents on the phenyl radical(s) may be selected from, for example, alkoxy and alkyl groups containing up to 4 carbon atoms (e.g. methoxy and/or methyl group(s)) and the nitro group; the symbol $R^1$ may represent, for example, a benzyl or p-methoxybenzyl group. Cycloalkyl groups within the definitions of symbols $R^1$ and $R^2$ contain 3 to 8, preferably 6, carbon atoms. The compounds may be provided as salts or prodrugs, particularly alkali metal salts when $R^1$ is H. See, e.g., U.S. Pat. No. 5,260,291.

Temozolomide, in oral dosage form as 5 mg, 20 mg, 100 mg, and 250 mg capsules, is commercially available as TEMODAR™ from Schering Corporation, Kenilworth N.J. 07033 USA.

Alkylating agents may be prepared in pharmaceutically acceptable formulations in like manner as described above, in the same or different formulation that contains the tumor vaccine, e.g., EGFRvIII peptide.

In a preferred embodiment, the alkylating agent is administered in a cycle of daily doses for 3, 4, 5, 6 or 7 consecutive days. A suitable daily dose may be from 50, 100 or 150 mg/m²/dose, up to 200, 250 or 300 mg/m²/dose. This cycle may be repeated, e.g., every two, three, four or five weeks, for up to a total of 6, 8, or 10 cycles. The first dose in the first cycle of alkylating agent may be administered at any suitable point in time. In some embodiments the first dose of alkylating agent is administered up to two or four weeks before administration of the immunotherapeutic agent; in some embodiments the first dose of alkylating agent is administered at least two, four or six weeks following the administration of the immunotherapeutic agent. Additional schedules of administration may be included where additional therapeutic treatments such as external beam radiotherapy are also applied to the subject.

Optionally, the subject may also receive external beam radiotherapy. For example, external beam radiotherapy may be utilized for brain tumors such as glioblastoma. External beam radiotherapy is known and can be carried out in accordance with known techniques The beam can be generated by any suitable means, including medical linear accelerators and Cobalt 60 external beam units. The radiation source can be mounted in a gantry that rotates around the patient so that a target area within the patient is irradiated from different directions. Before irradiation the treatment is typically planned on a computer using algorithms that simulate the radiation beams and allow the medical personnel to design the beam therapy. Numerous variations of external beam therapy that can be used to carry out the present invention will be readily apparent to those skilled in the art. See, e.g., U.S. Pat. Nos. 6,882,702; 6,879,659; 6,865,253; 6,863,704; 6,826,254; 6,792,074; 6,714,620; and 5,528,650.

External beam therapy is preferably administered in a series of sessions in accordance with known techniques, with the sessions preferably beginning two to four weeks after administration of the immunotherapeutic agent. For example, the external beam radiotherapy may be administered 3, 4, 5, 6 or 7 days a week, over a period of four, five, six or seven weeks, at a daily dose of 0.5 or 1 Gy, up to 2 or 3 Gy, until the total desired dose (e.g., 30 or 40 Gy, up to 50 or 60 Gy) is administered.

The delivered dose may be to an area including a margin of normal tissue (e.g., ~1, 2 or 3 cm margin in all directions) around the tumor, or where the tumor or a portion thereof has previously been surgically removed, around the site of the tumor.

Where external beam radiotherapy is employed, the patient may receive an additional schedule of chemotherapeutic agent administration, different from that described above, at a somewhat lower dose, during the course of the radiotherapy. For example, the patient may receive daily doses of chemotherapeutic agent, e.g., alkylating agent in an amount of from 25 or 50 mg/m2/dose up to 100 or 125 mg/m²/dose daily during the course of the external beam therapy.

Examples of tumor antigens which can be used as anti-tumor vaccines include but are not limited to Cyclin-dependent kinase 4; β-catenin; Caspase-8; MAGE-1; MAGE-3; Tyrosinase; Surface Ig idiotype; Her-2/neu Receptor; MUC-1; HPV E6 and E7; CD5 Idiotype CAMPATH-1, CD20; Cell surface glycoprotein CEA, mucin-1; Cell surface carbohydrate Lewis$^x$; CA-125; Epidermal growth factor receptor; p185HER2; IL-2R; FAP-α; Tenascin; and metalloproteinases. EGFRvIII is exemplary of tumor-specific antigens. Cells which express these antigens can also be used as vaccines. Preferably the cells are killed prior to administration. The cells can be fractionated so that a fraction enriched for the tumor antigen is used as a vaccine. These antigens are merely exemplary and are not intended to be a comprehensive of the many useful antigens known in the art or which may be used.

Multiple preclinical model systems have demonstrated that the depletion of immune cell subsets can abrogate the efficacy of several types of immunotherapeutic approaches (Heimberger et al., 2003) indicating that chemotherapy administered during the effector stages of immunotherapy may be deleterious to efficacy. However, this does not preclude utilizing these agents together when appropriately timed to minimize the aforementioned effects. Furthermore, although applicants do not wish to be bound by any particular theory regarding mechanism of action, the depletion of certain effector cells, such as Tregs, may be a highly desirable outcome of chemotherapy yielding greater immunotherapeutic efficacy or may promote a desirable cytokine profile for adequate tumor control.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

To test the hypothesis that chemotherapy and immunotherapy can be administered concurrently, we treated a patient with a newly diagnosed GBM using the standard of care, temozolomide, while also administering a peptide vaccine targeting the epidermal growth factor variant III (EGFRvIII) (Heimberger et al., 2006). The amplification of the epidermal growth factor receptor (EGFR) gene, which results in over expression of the EGFR, a transmembrane tyrosine kinase receptor (Ekstrand et al., 1991) is associated with the mutant EGFR gene, EGFRvIII (Wikstrand et al., 1997). Previous work has shown that EGFR amplification is evident in all GBMs expressing EGFRvIII (Heimberger et al., 2005) and GBMs lacking the amplified EGFR are not positive for EGFRvIII protein (Aldape et al., 2004).

In May of 2005, a 51-year-old Caucasian man was evaluated following complaints of a three-week history of persistent morning headaches without associated nausea. A magnetic resonance (MR) image revealed a multi-lobular, irregularly enhancing lesion measuring 6.6×5.3×4.3 in the anterior aspect of the right temporal lobe. The sylvian fissure was bowed upward and there was 6 mm of midline shift. The patient underwent a gross total resection, with histology demonstrating a biphasic glioblastoma and malignant sarcoma. These components were confirmed by positive immunohistochemistry in the glioblastoma component with glial-fibrillary astrocytic protein (GFAP) and abundant reticulin production in the sarcoma component. A trichrome stain confirmed the biphasic nature of the tumor. EGFR-528 and EGFRvIII antibody immunohistochemistry staining was positive (Heimberger et al., 2005), with the EGFRvIII staining demonstrating strong diffuse reactivity, while the EGFR-528 staining was more focal. PTEN was strongly positive and p53 reactivity was present in more than 30% of tumor nuclei. The methylguanine-DNA methyltransferase (MGMT) DNA-repair gene was methylated (Hegi et al., 2005).

Post-operatively the patient underwent conventional external beam radiotherapy of 6000 cGy in 30 fractions. Concurrent temozolomide at 75 mg/m2 was administered during radiotherapy (Stupp et al., 2005). An MR image taken at the completion of radiotherapy was unchanged and demonstrated no evidence of progression. The patient then underwent a leukapheresis to obtain sufficient cells for immunological monitoring purposes. The patient received three intradermal (i.d.) injections of PEPvIII-3 (LEEKKGNYVVTDHC) (SEQ ID NO: 3)), conjugated to keyhole limpet hemocyanin (KLH) at a 1:1 ratio (w/w) (PEPvIII-KLH) (500 µg/immunization) with granulocyte-macrophage colony-stimulating factor (GM-CSF) (142 µg/immunization) every two weeks over an interval of 6 weeks (the induction phase). Thereafter, he underwent a second leukapheresis for immunological monitoring purposes. At this point, the patient began maintenance cycles of temozolomide of 150 mg/m2 on day 1-5. Beginning on day 19 of each cycle, complete blood counts were monitored every other day until there was evidence of recovery of the white blood cell count nadir. At nadir recovery, the patient received the vaccine i.d., usually on day 23 (range=19-25) of his 28-day cycle.

EXAMPLE 2

Delayed type hypersensitivity (DTH) testing to common recall antigens and the components of the vaccine were evaluated prior to the start of the vaccines, after the 3rd vaccine and monthly during his maintenance cycle on day 26. Prior to the start of the vaccine and after the completion of radiation and concurrent temozolomide the patient was only reactive to *Candida* and had no DTH reaction to the components of the vaccine, PEPvIII or KLH. However, after the 3rd vaccination, the patient became responsive to the KLH component of the vaccine. After the 10th vaccination, and while receiving concurrent temozolomide, he became reactive to the PEPvIII component of the vaccine. For comparison, of the patients that received the vaccine without cycled temozolomide (n=22), less than 15% ever became reactive to the PEPvIII component. After the most recent follow-up and administration of the 14th vaccination, the patient was markedly indurated (16×15 mm) at the PEPvIII DTH site. This would indicate that the temozolomide did not negatively influence the development of DTH responses in this particular patient.

EXAMPLE 3

To determine if PEPvIII-specific humoral responses were induced, serum was obtained from the patient monthly and was stored at −20° C. before analysis in a PEPvIII-Dynabead® assay. PEPvIII or the extracellular domain of EGFRvIII (EGFRvIII-ECD) were covalently linked to magnetic microspheres that were used to capture specific antibodies from patient's serum (Invitrogen, Carlsbad, Calif.) according to the manufacturer's instructions. All serum samples are initially diluted 1:10 with phosphate-buffered saline (PBS)+0.5% bovine serum albumin (BSA) and assayed in triplicate. To determine specificity, an additional sample set was pre-incubated for 15 minutes with 500 ng of the PEPvIII peptide to block any anti-PEPvIII that would be captured by the PEPvIII conjugated Dynabeads. Standards of human-mouse chimeric anti-PEPvIII antibody (81-0.11 ng/ml) are run with each assay along with positive (patient sample ACT4) and negative (normal donor serum) controls. The flow cytometer was standardized with PE-FACS microbeads and un-reacted PEPvIII Dynabeads. Prior to the administration of the vaccine, there were no detectable humoral responses to the EGFRvIII. After the vaccination, there was a significant increase in IgG responses to EGFRvIII to a mean fluorescent intensity (MFI) of 13 and the humoral responses have been maintained despite administration the temozolomide.

EXAMPLE 4

To determine if CD8+ cytotoxic responses were induced to PEPvIII, the patient's peripheral blood mononuclear cells (PBMCs) from each leukapheresis and monthly PBMCs were stimulated with either tetanus toxoid (QYIKANSKFIGITE) (SEQ ID NO: 5) (10 µg/ml) (positive control), PEP-1 (HDTVYCVKGNKELE) (SEQ ID NO: 4) (10 µg/mL) (negative control), PEPvIII (10 µg/mL) (vaccine component), or KLH (10 µg/ml) (vaccine component). A negative control included un-stimulated cells. The corresponding isotype controls were used for each condition, including γ-interferon (IFN) secretion. All wells were incubated for 6 hr at 37° C. with Golgiplug™ (Pharmingen, San Diego, Calif.), a protein transport inhibitor that blocks the intracellular transport process. After incubation, the cells were washed and blocked for non-specific binding using purified anti-CD16 antibody (Pharmingen) and rabbit serum (Pharmingen). The cells were stained for surface markers (CD3, CD4, CD8) by incubating with the appropriate fluorescein-isothiocyanate and allophycocyanin labeled fluorescence-labeled primary antibody or isotype control (Pharmingen). Cells were then fixed with Cytofix/Cytoperm (BD Biosciences, San Jose, Calif.) and then incubated with phycoerythrin-labeled antibody against γ-IFN or the isotype control. After staining, cells were washed and a minimum of 1×10$^5$ live, gated events were assessed by flow cytometry on a FACSCalibur flow cytometer using Cellquest software (BD Immunocytometry systems, San Jose, Calif.). Prior to receiving the vaccine the patient had minimal response in the un-stimulated controls and with the PEP-1 negative control. After receiving the vaccine, and during administration of the temozolomide, there was an increase in PEPvIII-specific γ-IFN producing CD8$^+$ T cells.

EXAMPLE 5

To characterize the response of the various T cell populations during a cycle of temozolomide (5/21 schedule) and concurrently administered vaccine (day 19 on this example), we obtained peripheral blood on days 0, 3, 5, 12, 19, 23, 25 and 26. By flow analysis cytometry, we investigated the percentage of the CD8+ T cell and CD4+CD25+FoxP3+ regulatory T cells subsets during an immunochemotherapy cycle. All fluorescence-conjugated monoclonal antibodies (mAb) (PerCP-Cy5.5-CD3, FITC-CD8, APC-CD4 and PE-CD25) were purchased from BD Biosciences except the FITC-labeled mAb of FoxP3 was made by eBioscience. The surface and intracellular staining of peripheral blood cells were performed according to the standard procedures provided by the manufacturer. Results were analyzed by FACSCalibur flow cytometer using Cellquest Pro software (BD Biosciences). In contrast to the decline of the CD8+ T cell subset, the Treg population started to increase after the administration of temozolomide for 3 days and reached its peak (0.9% of total CD4+ T cells) on day 12. The Tregs then began to drop until day 23 while the CD8+ T cell numbers started to recover. At the end of the course, both of CD8+ T cell and Treg populations recovered to pre-treatment levels. The vaccination resulted in a boost of CD8+ cytotoxic T cells during a period of relative diminished Tregs.

EXAMPLE 6

Over the last 15 months, the patient underwent complete physical examination and brain MR imaging at two-month intervals. His exam has remained stable and MR imaging has failed to demonstrate any evidence of recurrence. He works full time without impairment and has a Karnofsky performance status (KPS) of 100% and mini-mental status exam score of 30/30. His neurological exam is completely normal.

This report suggests that concurrent administration of chemotherapy with immunotherapy may be possible if the timing of the treatments are carefully monitored. In the case reported, there are several findings that indicate that the co-administration of the temozolomide has not affected the efficacy of the PEPvIII-KLH vaccine. First, the patient has not yet progressed at 15 months of follow-up. This was the median TTP for patients (n=22) that received only vaccination therapy. Thus, the clinical efficacy does not appear to have been effected compared to patients that did not receive the concurrently administered temozolomide. The patient developed DTH responses to the PEPvIII component of the vaccine, even while receiving temozolomide, whereas only 15% of the patients receiving the vaccine alone developed these types of responses. Furthermore, the area of PEPvIII DTH reactivity has continued to increase with subsequent vaccinations. Third, IgG specific responses to PEPvIII were induced after the 3rd vaccination and have been maintained while receiving the concurrent temozolomide. Fourth, the induced PEP-3 specific CD3+CD8+γ-IFN producing T cells do not appear to be diminished during cycles of concurrently administered temozolomide but appear enhanced during the concurrently administered temozolomide. Finally, we have followed the CD8+ T cell and Treg populations during a single treatment cycle and found that there appears to be a window of T effector (CD8+ T cell) responsiveness with a relative diminution of Tregs. Thus, the concurrent administration of temozolomide and vaccine does not appear to diminish the induced immune responses, in the manner in which we have described.

The use of lymphodepletion to augment immunological responses has been described in both murine model systems (Berenson et al., 1975; Cheever et al., 1980; North, 1982) and in human cancer patients (Dudley et al., 2002; Dudley et al., 2005). Multiple mechanisms have been proposed to be responsible for these enhanced anti-tumor responses. Lymphodepletion may remove competition at the surface of antigen presenting cells (Kedl et al., 2000), enhance the availability of cytokines such as IL-7 and IL-15, which augment T cell activity (Gattinoni et al., 2005) and deplete the immune inhibitory Tregs (Anthony et al., 2005). Chemotherapy could also potentially augment immunological responsiveness by enhancing immune priming and presentation (Nowak et al., 2002), enhancing antigen expression (Aquino et al., 1998), and enhancing targets for immune eradication (Ciusani et al., 2002). When a vaccination is administered during the nadir of temozolomide, we hypothesized that there may be an enhanced effector response. Those effector responses may be secondary to a lag in the recovery of Tregs thus allowing a greater clonotypic expansion than would have otherwise been seen without the temozolomide. This was certainly observed during a monitored chemoimmunotherapy cycle on this particular patient. The lag of recovery of Tregs relative to effector T cells is not surprising given the normal physiological roles of immune cell responses. In order to mount an immune response, T effectors would need to become activated, proliferate and mediate their response. If this remained unchecked by homeostatic mechanisms such as Tregs, then the T cell proliferation would escalate unabated. Therefore, the delay of Treg response would allow for efficacious immune responses but eventual down-modulation/regulation of this response.

In conclusion, this case report suggests that co-administration of chemotherapy and immunotherapy may not be deleterious.

REFERENCES

The disclosure of each reference cited is expressly incorporated herein.

Hatano, M., J. Eguchi, et al. (2005). "EphA2 as a glioma-associated antigen: a novel target for glioma vaccines." *Neoplasia* 7(8): 717-22.

Liu, G., J. S. Yu, et al. (2004). "AIM-2: a novel tumor antigen is expressed and presented by human glioma cells." *J Immunother* 27(3): 220-6.

Liu, M., B. Dai, et al. (2006). "FoxM1B is overexpressed in human gliobastomas and critically regulates the tumorigenicity of glioma cells." *Can Res* 66(7): 3593-3602.

Xie, D., Y. X. Zeng, et al. (2006). "Expression of cytoplasmic and nuclear survivin in primary and secondary human glioblastoma." *Br J Cancer* 94(1): 108-114.

We claim:

1. A method of treating a tumor expressing EGFRvIII in a subject, comprising the steps of:
   administering to the subject an amount of an EGFRvIII peptide effective to induce an IgG response to EGFRvIII peptide or to induce EGFRvIII peptide-specific γ-IFN producing CD8$^+$ T cells, after administering an amount of temozolomide or a pharmaceutically acceptable salt thereof effective to induce lymphopenia of CD8+ T cells; wherein the EGFRvIII peptide is administered after the CD8+ T cells begin to recover from nadir of the induced lymphopenia, and wherein the combined administration of the peptide and the temozolomide or pharmaceutically acceptable salt thereof increases immunotherapeutic efficacy.

2. A method of treating a tumor expressing EGFRvIII in a subject, comprising the steps of:
   administering to the subject an amount of an EGFRvIII peptide conjugated to KLH effective to induce an IgG response to EGFRvIII peptide or to induce EGFRvIII peptide-specific γ-IFN producing CD8$^+$ T cells after administering to the subject an amount of temozolomide or a pharmaceutically acceptable salt thereof effective to induce lymphopenia of CD8+ T cells, wherein the EGFRvIII peptide is administered after the CD8+T cells begin to recover from nadir of the induced lymphopenia; and
   administering to the subject GM-CSF as an adjuvant in an effective amount concurrently with the EGFRvIII peptide; wherein the combined administration of the peptide and the temozolomide or the pharmaceutically acceptable salt increases immunotherapeutic efficacy.

* * * * *